US012678141B2

(12) United States Patent
Miyachi

(10) Patent No.: US 12,678,141 B2
(45) Date of Patent: Jul. 14, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 92 days.

(21) Appl. No.: 18/359,571

(22) Filed: Jul. 26, 2023

(65) Prior Publication Data

US 2024/0081788 A1    Mar. 14, 2024

(30) Foreign Application Priority Data

Sep. 12, 2022    (JP) .................................. 2022-144557

(51) Int. Cl.
*A61B 8/08*       (2006.01)
*A61B 8/00*       (2006.01)

(52) U.S. Cl.
CPC ............ *A61B 8/5207* (2013.01); *A61B 8/085* (2013.01); *A61B 8/469* (2013.01)

(58) Field of Classification Search
CPC ....... A61B 8/5207; A61B 8/085; A61B 8/469; A61B 8/0833
See application file for complete search history.

(56) References Cited

U.S. PATENT DOCUMENTS 5,984,870 A    11/1999   Giger et al.
2013/0144167 A1*   6/2013   Lee ...................... A61B 8/5215
                                       600/443

2015/0320383 A1*   11/2015   Dunmire .............. A61B 8/0875
                                       600/443
2017/0156702 A1   6/2017   Park et al.
2020/0178846 A1   6/2020   Matsumoto
(Continued)

FOREIGN PATENT DOCUMENTS

JP     H06-125902 A    5/1994
JP     H08-131436 A    5/1996
(Continued)

OTHER PUBLICATIONS

The extended European search report issued by the European Patent Office on Dec. 11, 2023, which corresponds to European Patent Application No. 23195799.4-1126 and is related to U.S. Appl. No. 18/359,571.

(Continued)

*Primary Examiner* — Kaitlyn E Sebastian
(74) *Attorney, Agent, or Firm* — Studebaker Brackett PLLC

(57) ABSTRACT

Provided are a control method for an ultrasound diagnostic apparatus and an ultrasound diagnostic apparatus that enable a user to easily and accurately perform a diagnosis.

An ultrasound diagnostic apparatus includes: a detection target detection unit configured to detect a detection target captured in an ultrasound image; a detection target analysis unit configured to analyze the detection target detected by the detection target detection unit; and a region-of-interest setting unit configured to set, on the ultrasound image, a region of interest that includes the detection target and that is to be disposed at a position corresponding to an analysis result of the detection target by the detection target analysis unit.

18 Claims, 8 Drawing Sheets

(56) References Cited

U.S. PATENT DOCUMENTS

2021/0015447 A1 *  1/2021  St. Pierre ........... A61B 10/0233
2021/0219941 A1     7/2021  Tsutaoka

FOREIGN PATENT DOCUMENTS

WO        2019/039028 A1    2/2019
WO     WO-2020075609 A1 *  4/2020   .............. A61B 8/08

OTHER PUBLICATIONS

Communication pursuant to Article 94(3) EPC issued by the European Patent Office on Jan. 10, 2025, which corresponds to European Patent Application No. 23195799.4-1122 and is related to U.S. Appl. No. 18/359,571.
"Notice of Reasons for Refusal" Office Action issued in JP 2022-144557; mailed by the Japanese Patent Office on Mar. 3, 2026.

* cited by examiner

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

The present application claims priority under 35 U.S.C. § 119 to Japanese Patent Application No. 2022-144557, filed on Sep. 12, 2022. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus for setting a region of interest in an ultrasound image.

2. Description of the Related Art

Conventionally, an ultrasound image representing a tomogram of an inside of a subject under examination has been acquired using a so-called ultrasound diagnostic apparatus, and an examination for the subject under examination has been performed by a user such as a doctor based on the acquired ultrasound image. In order for the user to smoothly perform such an examination for the subject under examination, there is known a technique for automatically detecting or measuring an object such as an organ of the subject under examination shown in an ultrasound image. In this case, a so-called region of interest may be set in the ultrasound image in order to limit a range in which processing such as automatic detection or measurement is performed and to smoothly perform the processing. For example, WO2019/039028A discloses that a rectangular region of interest is set in an ultrasound image in order to limit a range in which a detection target is detected.

SUMMARY OF THE INVENTION

Meanwhile, in a case where a user such as a doctor confirms a detection target shown in an ultrasound image and performs a diagnosis, a region of interest including the detection target in the ultrasound image may be displayed on a monitor such that the detection target can be easily confirmed. Usually, the region of interest is often displayed with a closed rectangular frame line.

In addition, in a case where the detection target is a feces, a cyst, or the like present inside the rectum, it is known that in order to perform an accurate diagnosis, it is necessary to confirm not only the presence of the detection target but also whether or not there is a so-called posterior acoustic shadow in a region located at a deeper part than the detection target, whether or not a so-called posterior echo is enhanced, or the like. Therefore, in a case where the region of interest is displayed with the closed rectangular frame line, it may be difficult for the user to confirm the region located at the deeper part than the detection target in the ultrasound image, which may make it difficult to easily perform an accurate diagnosis.

The present invention has been made in order to solve such a conventional problem, and an object of the present invention is to provide an ultrasound diagnostic apparatus and a control method for an ultrasound diagnostic apparatus that enable a user to easily and accurately perform a diagnosis.

According to the following configuration, the above object can be achieved.

[1] An ultrasound diagnostic apparatus comprising:
a detection target detection unit configured to detect a detection target captured in an ultrasound image;
a detection target analysis unit configured to analyze the detection target detected by the detection target detection unit; and
a region-of-interest setting unit configured to set, on the ultrasound image, a region of interest that includes the detection target and that is to be disposed at a position corresponding to an analysis result of the detection target by the detection target analysis unit.

[2] The ultrasound diagnostic apparatus according to [1],
in which the detection target analysis unit is configured to analyze a property of a posterior echo of the detection target, and
the region-of-interest setting unit is configured to change a position of the region of interest relative to the detection target according to the property of the posterior echo of the detection target analyzed by the detection target analysis unit.

[3] The ultrasound diagnostic apparatus according to [2],
in which the region-of-interest setting unit is configured to set a first region of interest in a case where an enhancement of the posterior echo of the detection target analyzed by the detection target analysis unit is equal to or higher than a predetermined level, and to set a second region of interest of which a position relative to the detection target is different from that of the first region of interest in a case where the enhancement of the posterior echo of the detection target analyzed by the detection target analysis unit is less than the predetermined level.

[4] The ultrasound diagnostic apparatus according to [1],
in which the region-of-interest setting unit is configured to set a first region of interest in a case where the detection target analyzed by the detection target analysis unit is a feces inside a rectum, and to set a second region of interest of which a position relative to the detection target is different from that of the first region of interest in a case where the detection target analyzed by the detection target analysis unit is an empty rectum.

[5] The ultrasound diagnostic apparatus according to [1],
in which the region-of-interest setting unit is configured to set a first region of interest in a case where the detection target analyzed by the detection target analysis unit is a cyst, and to set a second region of interest of which a position relative to the detection target is different from that of the first region of interest in a case where the detection target analyzed by the detection target analysis unit is a tumor.

[6] An ultrasound diagnostic apparatus comprising:
a mode input unit configured to input an examination mode for a detection target captured in an ultrasound image; and
a region-of-interest setting unit configured to set, on the ultrasound image, a region of interest including the detection target,
in which the region-of-interest setting unit is configured to set the region of interest to be disposed at a position corresponding to the examination mode input from the mode input unit.

[7] The ultrasound diagnostic apparatus according to [6], in which the region-of-interest setting unit is configured to set a first region of interest in a case where the examination mode input from the mode input unit indicates a feces inside a rectum as the detection target or a cyst as the detection target, and to set a second region of interest of which a position relative to the detection target is different from that of the first region of interest in a case where the examination mode input from the mode input unit indicates an empty rectum as the detection target or a tumor as the detection target.

[8] The ultrasound diagnostic apparatus according to any one of [3] to [5] and [7], in which the first region of interest is a region having a position relative to the detection target such that the detection target is located in an upper part within the first region of interest, and the second region of interest is a region having a position relative to the detection target such that the detection target is located in a central part within the second region of interest.

[9] The ultrasound diagnostic apparatus according to any one of [3] to [5], [7], and [8], in which the first region of interest has a length in a depth direction of at least 2 times and no more than 5 times a length of the detection target, and the second region of interest has a length in a depth direction of at least 1 time and less than 2 times the length of the detection target.

[10] The ultrasound diagnostic apparatus according to any one of [1] to [9], further comprising:
an ultrasound probe; and
an image acquisition unit configured to acquire the ultrasound image using the ultrasound probe.

[11] A control method for an ultrasound diagnostic apparatus, comprising:
detecting a detection target captured in an ultrasound image;
analyzing the detected detection target; and
setting, on the ultrasound image, a region of interest that includes the detection target and that is to be disposed at a position corresponding to an analysis result of the detection target.

[12] A control method for an ultrasound diagnostic apparatus, comprising:
inputting an examination mode for a detection target captured in an ultrasound image; and
setting, on the ultrasound image, a region of interest that includes the detection target and that is to be disposed at a position corresponding to the input examination mode.

According to the present invention, there is provided an ultrasound diagnostic apparatus comprising: a detection target detection unit configured to detect a detection target captured in an ultrasound image; a detection target analysis unit configured to analyze the detection target detected by the detection target detection unit; and a region-of-interest setting unit configured to set, on the ultrasound image, a region of interest that includes the detection target and that is to be disposed at a position corresponding to an analysis result of the detection target by the detection target analysis unit. Alternatively, there is provided an ultrasound diagnostic apparatus comprising: a mode input unit configured to input an examination mode for a detection target captured in an ultrasound image; and a region-of-interest setting unit configured to set a region of interest including the detection target on the ultrasound image, in which the region-of-interest setting unit is configured to set the region of interest to be disposed at a position corresponding to the examination mode input from the mode input unit. Therefore, the user can easily and accurately perform a diagnosis.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment 1

Figure 1:
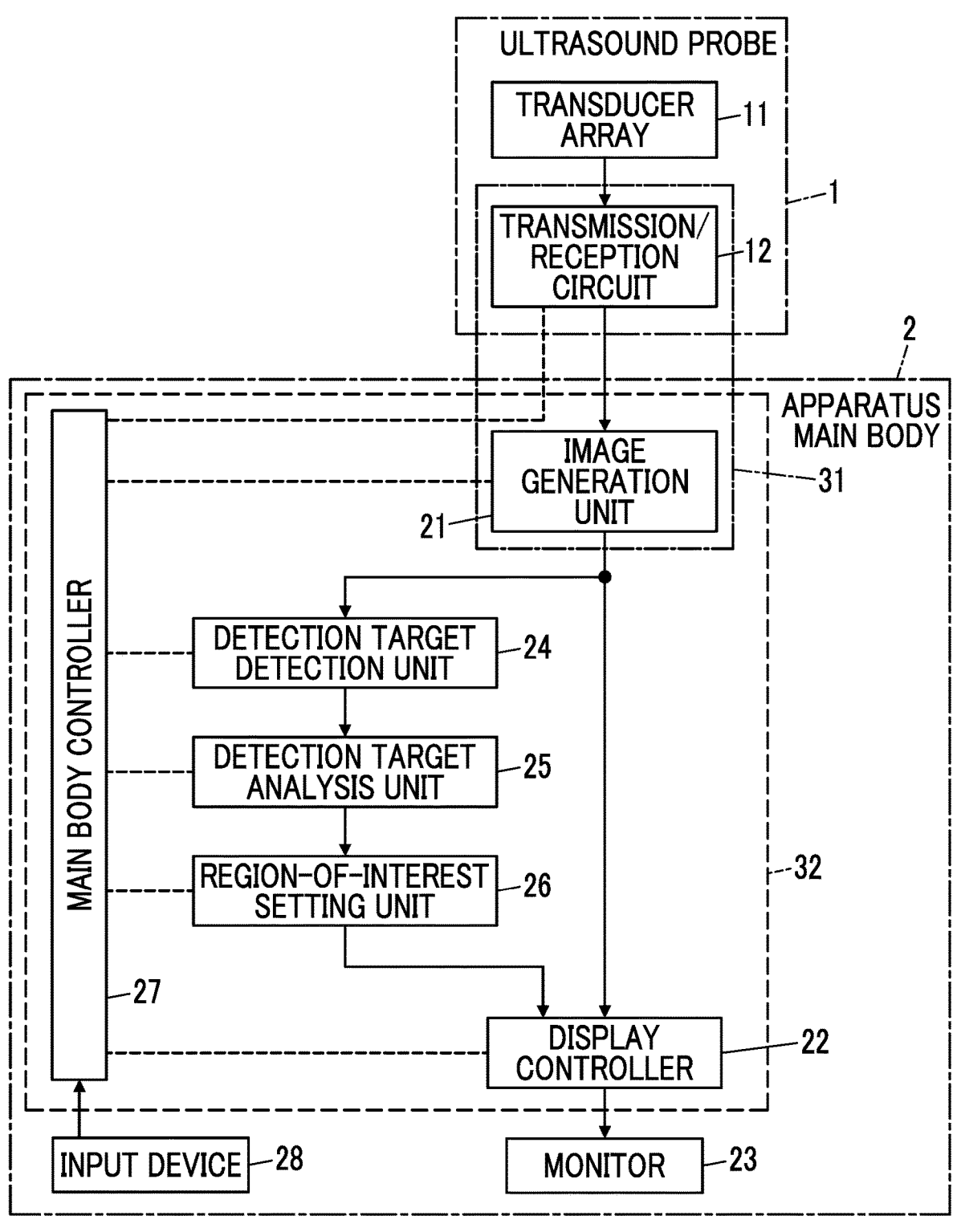
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1 and an apparatus main body 2 connected to the ultrasound probe 1.

The ultrasound probe 1 includes a transducer array 11. A transmission/reception circuit 12 is connected to the transducer array 11.

The apparatus main body 2 includes an image generation unit 21 connected to the transmission/reception circuit 12 of the ultrasound probe 1. A display controller 22 and a monitor 23 are sequentially connected to the image generation unit 21. In addition, a detection target detection unit 24, a detection target analysis unit 25, and a region-of-interest setting unit 26 are sequentially connected to the image generation unit 21. The region-of-interest setting unit 26 is connected to the display controller 22. In addition, a main body controller 27 is connected to the transmission/reception circuit 12, the image generation unit 21, the display controller 22, the detection target detection unit 24, the detection target analysis unit 25, and the region-of-interest setting unit 26. An input device 28 is connected to the main body controller 27.

In addition, the transmission/reception circuit 12 and the image generation unit 21 constitute an image acquisition unit 31. Further, the image generation unit 21, the display controller 22, the detection target detection unit 24, the detection target analysis unit 25, the region-of-interest setting unit 26, and the main body controller 27 constitute a processor 32 for the apparatus main body 2.

The transducer array 11 of the ultrasound probe 1 includes a plurality of ultrasound transducers one-dimensionally or two-dimensionally arranged. Each of these ultrasound transducers transmits an ultrasound wave in accordance with a drive signal supplied from the transmission/reception circuit 12 and receives an ultrasound echo from a subject under examination to output a signal based on the ultrasound echo. For example, each ultrasound transducer is composed of a piezoelectric material consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like, and electrodes formed at both ends of the piezoelectric material.

Figure 2:
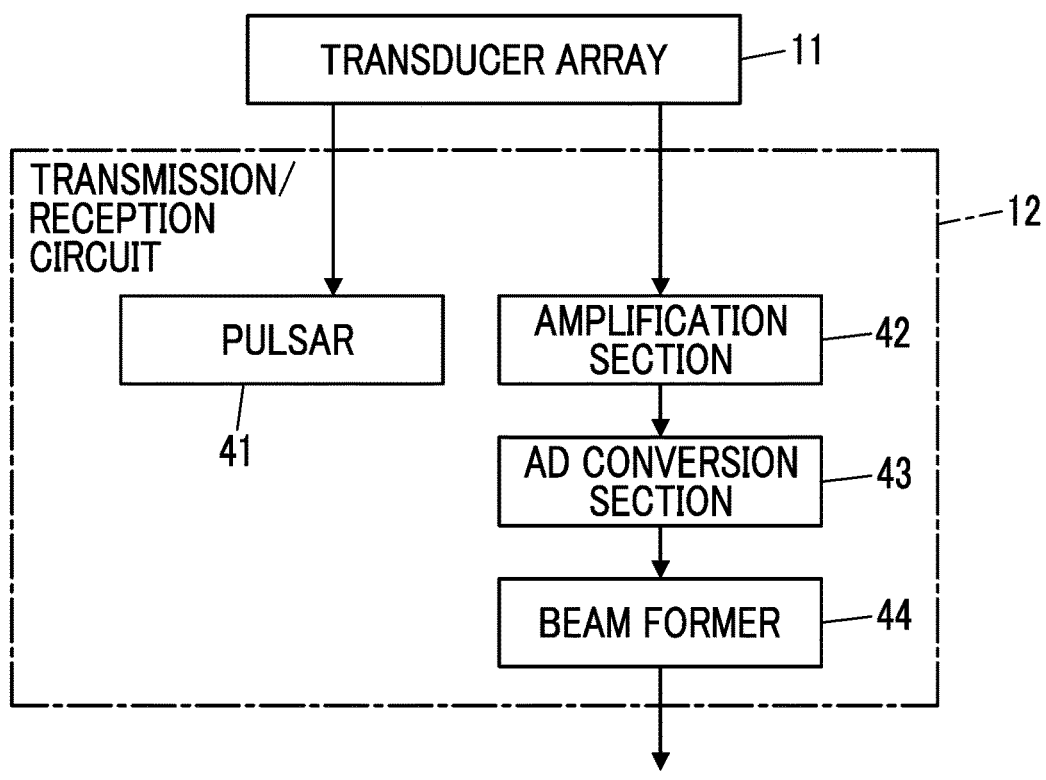
FIG. 2 is a block diagram showing a configuration of a transmission/reception circuit in Embodiment 1 of the present invention.

Under the control of the main body controller 27, the transmission/reception circuit 12 transmits the ultrasound wave from the transducer array 11 and generates a sound ray signal based on a reception signal acquired by the transducer array 11. As shown in FIG. 2, the transmission/reception circuit 12 includes a pulsar 41 connected to the transducer array 11, an amplification section 42, an analog-to-digital (AD) conversion section 43, and a beam former 44 that are sequentially connected in series to the transducer array 11.

The pulsar 41 includes, for example, a plurality of pulse generators, and the pulsar 41 adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the main body controller 27. In this way, in a case where a pulsed or continuous-wave voltage is applied to the electrodes of the ultrasound transducer of the transducer array 11, the piezoelectric material expands and contracts to generate pulsed or continuous-wave ultrasound wave from each of the ultrasound transducers, whereby an ultrasound beam is formed from the combined wave of these ultrasound waves.

The transmitted ultrasound beam is reflected in, for example, a target such as a site of the subject under examination and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 42.

The amplification section 42 amplifies the signal input from each of the ultrasound transducers constituting the transducer array 11 and transmits the amplified signal to the AD conversion section 43. The AD conversion section 43 converts the signal transmitted from the amplification section 42 into digital reception data. The beam former 44 performs so-called reception focus processing by applying and adding a delay to each reception data received from the AD conversion section 43. By this reception focus processing, each reception data converted by the AD conversion section 43 is phase-added, and a sound ray signal in which the focus of the ultrasound echo is narrowed down is acquired.

Figure 3:
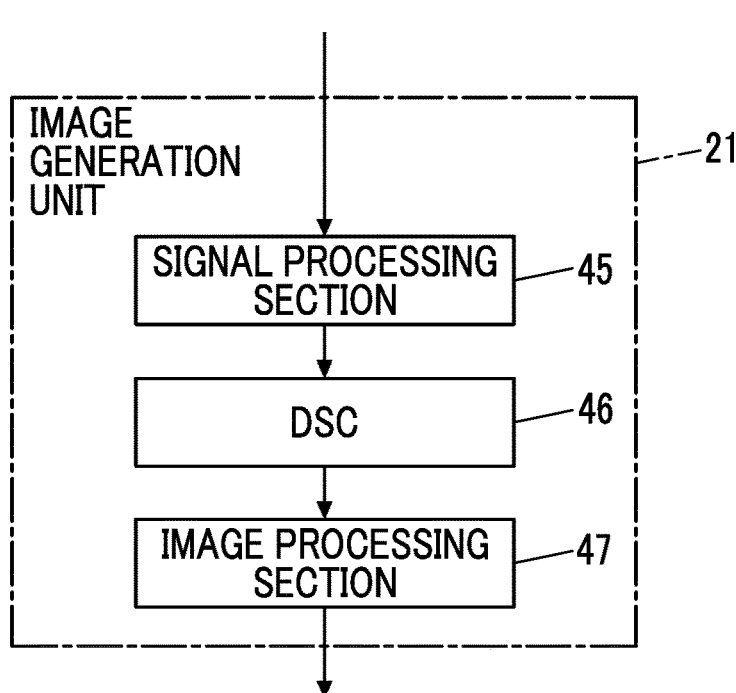
FIG. 3 is a block diagram showing a configuration of an image generation unit in Embodiment 1 of the present invention.

As shown in FIG. 3, the image generation unit 21 has a configuration in which a signal processing section 45, a digital scan converter (DSC) 46, and an image processing section 47 are sequentially connected in series.

The signal processing section 45 generates a B-mode image signal, which is tomographic image information regarding tissues inside the subject under examination, by performing, on the sound ray signal received from the transmission/reception circuit 12, correction of the attenuation due to the distance according to the depth of the reflection position of the ultrasound wave using a sound speed value set by the main body controller 27 and then performing envelope detection processing.

The DSC 46 converts (raster-converts) the B-mode image signal generated by the signal processing section 45 into an image signal according to a normal television signal scanning method.

The image processing section 47 performs various types of necessary image processing such as gradation processing on the B-mode image signal input from the DSC 46 and then sends the B-mode image signal to the display controller 22 and the detection target detection unit 24. Hereinafter, the B-mode image signal that has been subjected to image processing by the image processing section 47 is referred to as an ultrasound image.

Under the control of the main body controller 27, the display controller 22 performs predetermined processing on the ultrasound image or the like generated by the image generation unit 21 and displays the ultrasound image or the like on the monitor 23.

The monitor 23 performs various kinds of display under the control of the display controller 22. The monitor 23 can include a display device such as a liquid crystal display (LCD), or an organic electroluminescence (EL) display, for example.

The detection target detection unit 24 analyzes the ultrasound image generated by the image generation unit 21 to detect the detection target captured in the ultrasound image. The detection target detection unit 24 stores, for example, a plurality of template images for each of a plurality of detection targets and can detect the detection target by searching within the ultrasound image according to a so-called template matching method using the plurality of template images. In addition, the detection target detection unit 24 includes, for example, a machine learning model that has learned a large number of ultrasound images showing the plurality of detection targets, respectively, and can also use this machine learning model to detect the detection target shown in the ultrasound image.

Figure 4:
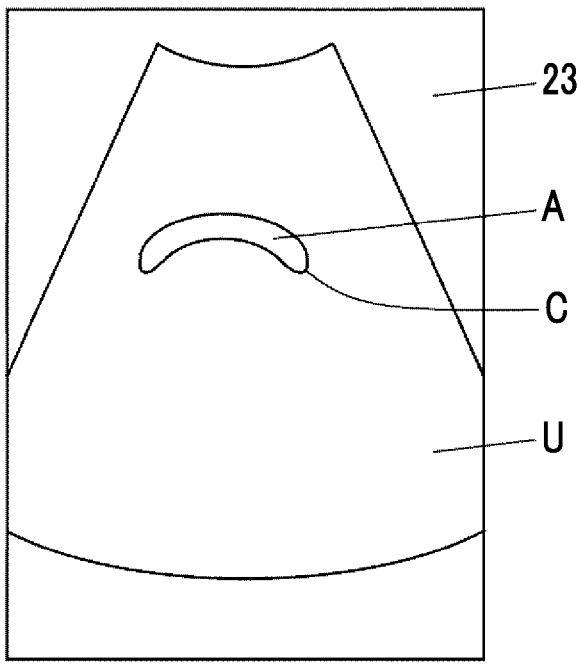
FIG. 4 is a diagram showing a contour line of a detection target.

For example, as shown in FIG. 4, the detection target detection unit 24 can output a contour line C of a detection target A in an ultrasound image U as a detection result.

Figure 5:
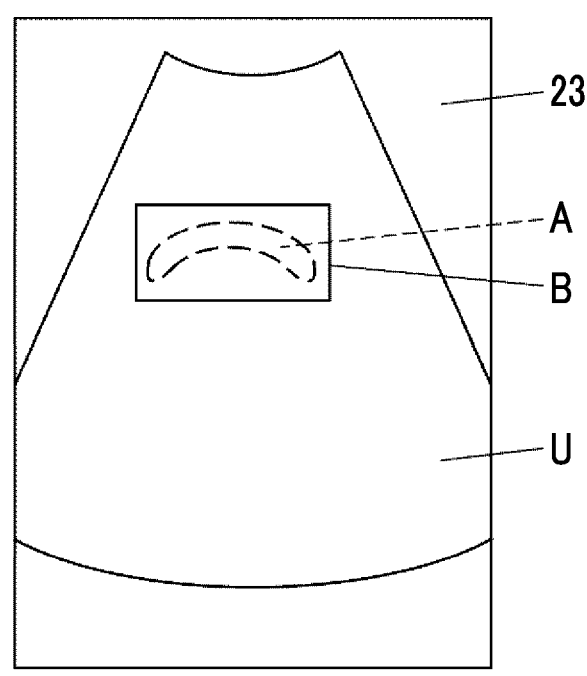
FIG. 5 is a diagram showing an image region including the detection target.

Instead of outputting the contour line C of the detection target A as the detection result, the detection target detection unit 24 can also output a rectangular image region B including the detection target A as the detection result, as shown in FIG. 5, for example. In this case, in order to accurately specify a position of the detection target A in a depth direction, it is preferable that a length of the image region B in the depth direction is at least 1 time and less than 2 times a length of the detection target A in the depth direction.

The detection target analysis unit 25 analyzes the detection target A detected by the detection target detection unit 24 and a property of a posterior echo thereof and determines whether or not there is a so-called posterior acoustic shadow, whether or not the posterior echo is enhanced, or the like in a region located at a deeper part than the detection target A in the ultrasound image U.

The posterior acoustic shadow refers to a low brightness region located at the deeper part than the detection target A in the ultrasound image U, which is caused by the ultrasound wave propagating from a body surface side of the subject under examination being unable to pass through the detection target A. The posterior acoustic shadow is often generated, for example, in the ultrasound image U in which a hard feces is captured. The enhancement of the posterior echo refers to a high brightness region located at the deeper part than the detection target A in the ultrasound image U, where the attenuation of the ultrasound wave is small, such as a cyst, for example. A user such as a doctor can accurately diagnose the subject under examination by grasping the property of such a region located at the deeper part than the detection target A.

Figure 6:
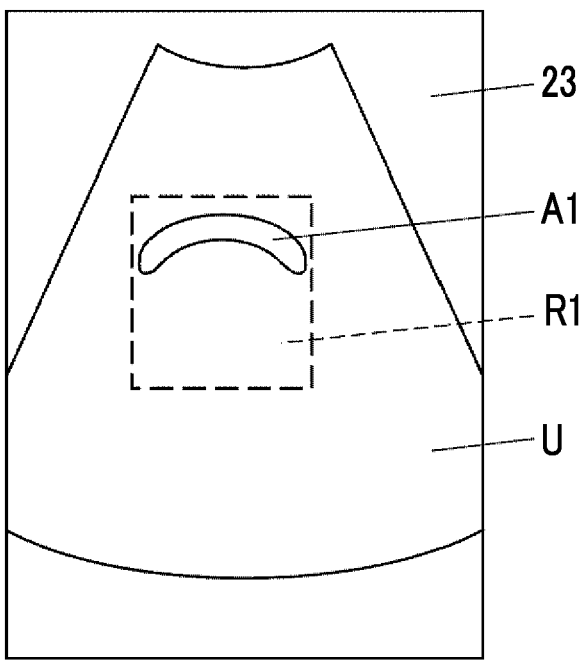
FIG. 6 is a diagram showing an example of a region of interest set for a feces shown in an ultrasound image.
Figure 7:
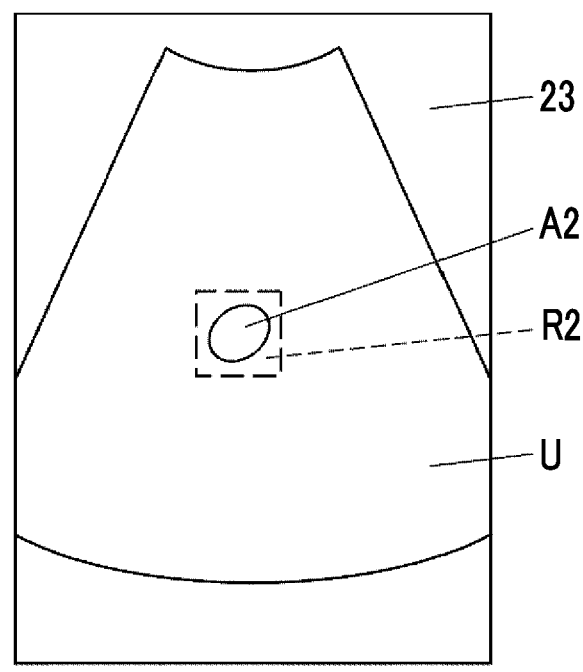
FIG. 7 is a diagram showing an example of a region of interest set for a rectum shown in the ultrasound image.

The region-of-interest setting unit 26 sets, on the ultrasound image U, a region of interest that includes the detection target and that is to be disposed at a position corresponding to the analysis result of the detection target A by the detection target analysis unit 25. In this case, the region-of-interest setting unit 26 can change a position of the region of interest relative to the detection target A according to the property of the posterior echo analyzed by the detection target analysis unit 25. For example, as shown in FIG. 6, the region-of-interest setting unit 26 can set, in a case where it is determined that there is a posterior acoustic shadow of a detection target A1 in the ultrasound image U, a rectangular first region of interest R1 having a position relative to the detection target such that the detection target is located in an upper part within the region of interest. In addition, for example, as shown in FIG. 7, the region-of-interest setting unit 26 can set, in a case where it is determined that there is no posterior acoustic shadow of a detection target A2 in the ultrasound image U, a rectangular second region of interest R2 having a position relative to the detection target A2 such that the detection target A2 is located in a central part within the region of interest.

FIG. 6 shows a feces inside the rectum as an example of the detection target A1 in which the posterior acoustic shadow can be confirmed. In addition, FIG. 7 shows an empty rectum as an example of the detection target A2 in which the posterior acoustic shadow cannot be confirmed.

In a case where the detection target detection unit 24 outputs the contour line C of the detection target A1, the region-of-interest setting unit 26 sets, for example, a rectangular region that includes the contour line C of the detection target A1 and that circumscribes the contour line C, enlarges the rectangular region by a magnification of at least 1 time and less than 2 times, for example, by a magnification of 1.2 times while fixing a position of the center of gravity of the rectangular region, and extends the rectangular region toward the deeper part along the depth direction such that the length of the rectangular region in the depth direction is at least 2 times and less than 5 times, for example, 3 times, the length of the detection target A1 in the depth direction, whereby the first region of interest R1 can be set.

Further, in a case where the detection target detection unit 24 outputs the contour line C of the detection target A2, the region-of-interest setting unit 26 sets, for example, a rectangular region that includes the contour line C and that circumscribes the contour line C, and enlarges the rectangular region by a magnification of at least 1 time and less than 2 times, for example, by a magnification of 1.2 times, while fixing the position of the center of gravity of the rectangular region, whereby the second region of interest R2 can be set.

In addition, in a case where the detection target detection unit 24 outputs the image region B including the detection target A1 instead of outputting the contour line C of the detection target A1, the region-of-interest setting unit 26 extends the image region B toward the deeper part along the depth direction such that the length of the image region B in the depth direction is at least 2 times and less than 5 times, for example, 3 times, the length of the detection target A1 in the depth direction, whereby the first region of interest R1 can be set.

In addition, in a case where the detection target detection unit 24 outputs the image region B including the detection target A2 instead of outputting the contour line C of the detection target A2, the region-of-interest setting unit 26 can set the image region B as the second region of interest R2.

The first region of interest R1 and the second region of interest R2 set in this manner are sent to the display controller 22 and are each displayed on the monitor 23, for example, with a closed frame line representing an edge of the region of interest. Since the first region of interest R1 including the region located at the deeper part than the detection target A1 is set for the detection target A1 such as a feces in which the posterior acoustic shadow can be confirmed, the user can easily and accurately perform a diagnosis by clearly confirming the posterior acoustic shadow of the detection target A1.

A case where the region-of-interest setting unit 26 enlarges each of the rectangular regions including the contour lines C of the detection targets A1 and A2 by a magnification of at least 1 time and less than 2 times in a case where the detection target detection unit 24 outputs the contour lines C of the detection targets A1 and A2 has been described, but it is preferable to perform enlargement processing by a magnification of larger than 1 time because enlarging the rectangular region including the contour line C by a magnification of larger than 1 time makes it easier for the user to confirm the detection target A1 or A2 in a case where the first region of interest R1 or the second region of interest R2 is displayed on the monitor 23.

In addition, for example, the region-of-interest setting unit 26 can set the first region of interest R1 in a case where the enhancement of the posterior echo of the detection target A analyzed by the detection target analysis unit 25 is equal to or higher than a predetermined level, and can set the second region of interest R2 in a case where the enhancement of the posterior echo of the detection target A analyzed by the detection target analysis unit 25 is less than the predetermined level. As a result, the user can clearly grasp whether or not the posterior echo is enhanced, and can easily and accurately perform the diagnosis. Examples of a detection target in which the enhancement of the posterior echo is easy to recognize include a cyst, and examples of a detection target in which the enhancement of the posterior echo is difficult to recognize include a tumor.

In addition, the region-of-interest setting unit 26 can set the first region of interest R1 in a case where the detection target A analyzed by the detection target analysis unit 25 is a feces inside the rectum, and can set the second region of interest R2 in a case where the detection target A analyzed by the detection target analysis unit 25 is an empty rectum. In a case where the detection target is a feces, the posterior acoustic shadow may be generated depending on the hardness of the feces. Therefore, by setting the first region of interest R1, the user can easily and accurately perform the diagnosis by confirming the ultrasound image U even in a case where the posterior acoustic shadow is generated.

In addition, the region-of-interest setting unit 26 can set the first region of interest R1 in a case where the detection target A analyzed by the detection target analysis unit 25 is a cyst, and can set the second region of interest R2 in a case where the detection target A analyzed by the detection target analysis unit 25 is a tumor. In a case where the detection target A is a cyst, the posterior echo is often enhanced. Therefore, by setting the first region of interest R1, the user can easily and accurately perform the diagnosis by confirming the ultrasound image U.

The main body controller 27 controls each unit of the apparatus main body 2 and the ultrasound probe 1 in accordance with a program recorded in advance, or the like.

The input device 28 accepts an input operation by an examiner and sends input information to the main body controller 27. The input device 28 is composed of, for example, a device for the examiner to perform an input operation, such as a keyboard, a mouse, a trackball, a touchpad, or a touch panel.

Although the processor 32 including the image generation unit 21, the display controller 22, the detection target detection unit 24, the detection target analysis unit 25, the region-of-interest setting unit 26, and the main body controller 27 may be composed of a central processing unit (CPU) and a control program for causing the CPU to perform various types of processing, the processor 32 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display controller 22, the detection target detection unit 24, the detection target analysis unit 25, the region-of-interest setting unit 26, and the main body controller 27 of the processor 32 can also be configured by being integrated partially or entirely into one CPU or the like.

Next, an example of an operation of the ultrasound diagnostic apparatus according to Embodiment 1 will be described with reference to the flowchart of FIG. 8.

First, in step S1, the ultrasound image U is acquired by the image acquisition unit 31. In this case, the transducer array 11 of the ultrasound probe 1 transmits the ultrasound beam into the subject under examination and receives the ultrasound echo from the inside of the subject under examination, whereby the reception signal is generated. The transmission/reception circuit 12 of the image acquisition unit 31 performs so-called reception focus processing on the reception signal to generate the sound ray signal, under the control of the main body controller 27. The sound ray signal generated by the transmission/reception circuit 12 is sent to the image generation unit 21. The image generation unit 21 generates the ultrasound image U using the sound ray signal sent from the transmission/reception circuit 12.

Next, in step S2, the detection target detection unit 24 analyzes the ultrasound image U acquired in step S1 to detect the detection target A shown in the ultrasound image U. In this case, the detection target detection unit 24 can detect the detection target A using a template matching method and can detect the detection target using a machine learning model that has learned in advance a large number of ultrasound images U showing the detection targets.

In step S3, the detection target analysis unit 25 analyzes the detection target A detected in step S2 and the property of the posterior echo thereof and determines whether or not there is the posterior acoustic shadow, whether or not the posterior echo is enhanced, or the like in the region located at the deeper part than the detection target A of the ultrasound image U.

Finally, in step S4, the region-of-interest setting unit 26 sets the first region of interest R1 or the second region of interest R2 according to the analysis result of the detection target analysis unit 25 in step S3.

For example, the region-of-interest setting unit 26 can set the first region of interest R1 in a case where it is determined in step S3 that there is the posterior acoustic shadow of the detection target A1 in the ultrasound image U, and can set the second region of interest R2 in a case where it is determined in step S3 that there is no posterior acoustic shadow of the detection target A2 in the ultrasound image U.

In addition, since examples of the detection target A1 in which the presence of the posterior acoustic shadow is easy to recognize include a feces inside the rectum and examples of the detection target A2 in which the presence of the posterior acoustic shadow is difficult to recognize include an empty rectum, the region-of-interest setting unit 26 can set the first region of interest R1 in a case where the detection target A analyzed by the detection target analysis unit 25 is a feces inside the rectum, and can set the second region of interest R2 in a case where the detection target A analyzed by the detection target analysis unit 25 is an empty rectum.

Further, for example, the region-of-interest setting unit 26 can set the first region of interest R1 in a case where the enhancement of the posterior echo of the detection target A analyzed by the detection target analysis unit 25 is equal to or higher than a predetermined level, and can set the second region of interest R2 in a case where the enhancement of the posterior echo of the detection target A analyzed by the detection target analysis unit 25 is less than the predetermined level.

Further, since examples of the detection target in which the enhancement of the posterior echo is easy to recognize include a cyst and examples of the detection target in which the enhancement of the posterior echo is difficult to recognize include a tumor, for example, the region-of-interest setting unit 26 can set the first region of interest R1 in a case where the detection target A analyzed by the detection target analysis unit 25 is a cyst, and can set the second region of interest R2 in a case where the detection target A analyzed by the detection target analysis unit 25 is a tumor.

The first region of interest R1 or the second region of interest R2 set in step S4 is sent to the display controller 22 and can be displayed on the monitor 23, for example, with a closed frame line representing the edge of each region of interest. Since the first region of interest R1 including the region located at the deeper part than the detection target A1 is set for the detection target A1 such as a feces in which the posterior acoustic shadow can be confirmed, the user can easily and accurately perform a diagnosis by clearly confirming the posterior acoustic shadow of the detection target A1.

Figure 8:
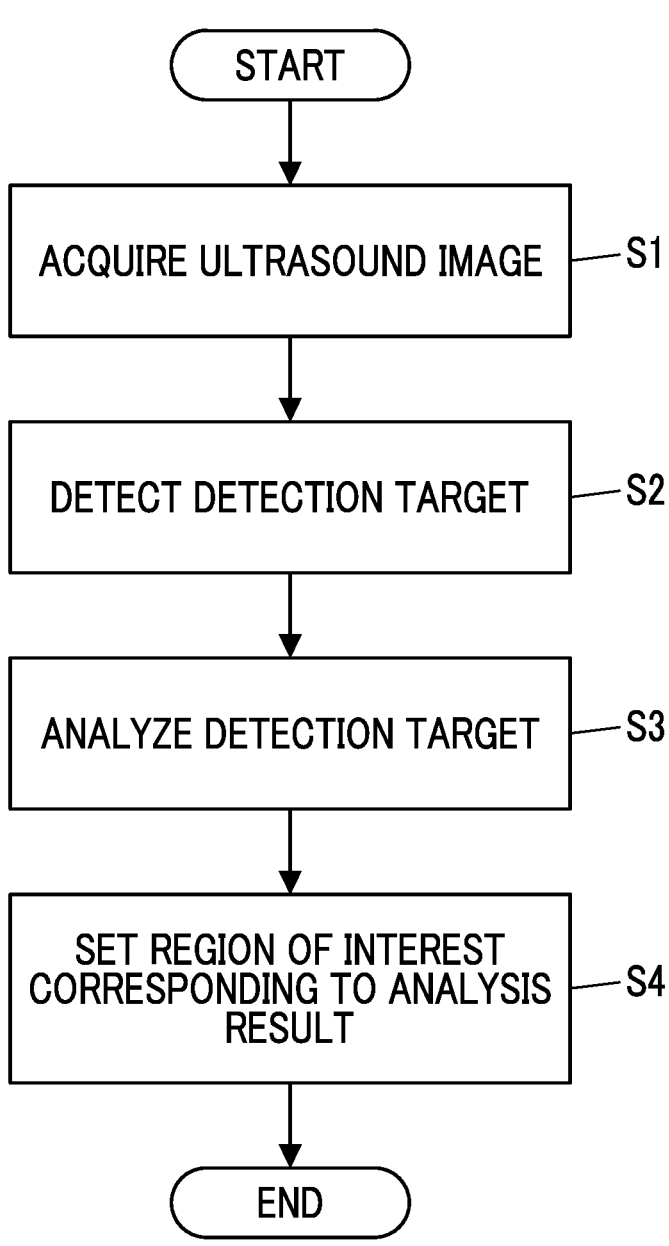
FIG. 8 is a flowchart showing an operation of the ultrasound diagnostic apparatus according to Embodiment 1 of the present invention.

In a case where the processing of step S4 is completed in this way, the operation of the ultrasound diagnostic apparatus shown in FIG. 8 is completed.

As described above, with the ultrasound diagnostic apparatus according to Embodiment 1 of the present invention, the detection target detection unit 24 detects the detection target A captured in the ultrasound image U, the detection target analysis unit 25 analyzes the detected detection target A, and the region-of-interest setting unit 26 sets the first region of interest R1 or the second region of interest R2 to be disposed at a position corresponding to the analysis result with respect to the position of the detection target. Therefore, even in a case where it is necessary to confirm the posterior echo of the detection target A, the user can easily and accurately perform a diagnosis related to the detection target A by clearly confirming the posterior echo.

Although a case where the transmission/reception circuit 12 is provided in the ultrasound probe 1 has been described, the transmission/reception circuit 12 may be provided in the apparatus main body 2.

Further, although a case where the image generation unit 21 is provided in the apparatus main body 2 has been described, the image generation unit 21 may be provided in the ultrasound probe 1.

In addition, the apparatus main body 2 may be a so-called stationary type, a portable type that is easy to carry, or a so-called handheld type that is composed of, for example, a smartphone or a tablet type computer. As described above, the type of the device that constitutes the apparatus main body 2 is not particularly limited.

In addition, the apparatus main body 2 can also comprise an image memory (not shown) that stores the ultrasound image U generated by the image generation unit 21 for each examination. In this case, the processing of steps S2 to S4 in the flowchart of FIG. 8 can also be performed, for example, on the ultrasound image U acquired in the past examination and stored in the image memory based on the user's instruction via the input device 28.

In addition, the apparatus main body 2 can also comprise an image input unit (not shown) for inputting the ultrasound image U from an external device (not shown). In this case, the processing of steps S2 to S4 in the flowchart of FIG. 8 can also be performed, for example, on the ultrasound image U input from the external device via the image input unit based on the user's instruction via the input device 28.

Further, a case where the first region of interest R1 and the second region of interest R2 set by the region-of-interest setting unit 26 each have a rectangular shape has been described, but the shape thereof is not limited to the rectangular shape and can be any shape, such as a circular shape and a polygonal shape.

Figure 9:
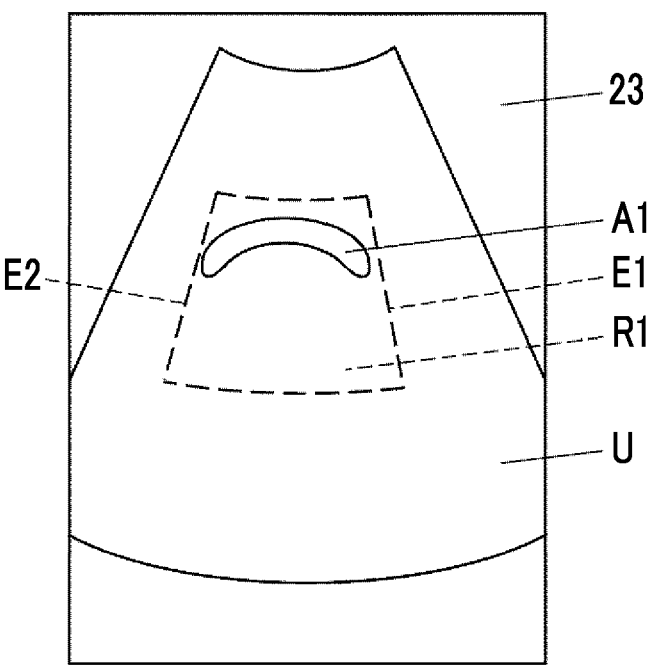
FIG. 9 is a diagram showing another example of the region of interest set for the feces captured in the ultrasound image.

In particular, the first region of interest R1 can have two sides E1 and E2 extending along the sound line of the ultrasound image U and facing each other, as shown in FIG. 9, for example. Since the posterior acoustic shadow generated in the region located at the deeper part than the detection target A1 is usually formed along the sound line, the first region of interest R1 has the two sides E1 and E2 extending along the sound line, so that the edge of the first region of interest R1 does not overlap with the posterior acoustic shadow, and the user can easily confirm the posterior acoustic shadow. In order to make it easier for the user to confirm the posterior echo even in a case where the posterior echo of the detection target A is enhanced, it is preferable for the first region of interest R1 to have the two sides E1 and E2 extending along the sound line because the posterior echo is formed along the sound line.

In addition, the second region of interest R2 can also have two sides E1 and E2 extending along the sound line of the ultrasound image U and facing each other, similarly to the first region of interest R1.

Further, a case where the first region of interest R1 and the second region of interest R2 are each displayed on the monitor 23 with a closed frame line representing the edge of the region of interest has been described, but the display modes of the first region of interest R1 and the second region of interest R2 are not particularly limited. For example, only a part of the line representing the edge of each of the first region of interest R1 and the second region of interest R2 may be displayed. For example, in a case where the first region of interest R1 and the second region of interest R2 each have a rectangular shape, only four corner portions of the line representing the edge of the rectangular shape can also be displayed.

Embodiment 2

In Embodiment 1, a case where the region of interest to be disposed at a position corresponding to the analysis result of the detection target A is set has been described, but in the ultrasound diagnostic apparatus, for example, a region of interest to be disposed at a position corresponding to a set examination mode can also be set.

Figure 10:
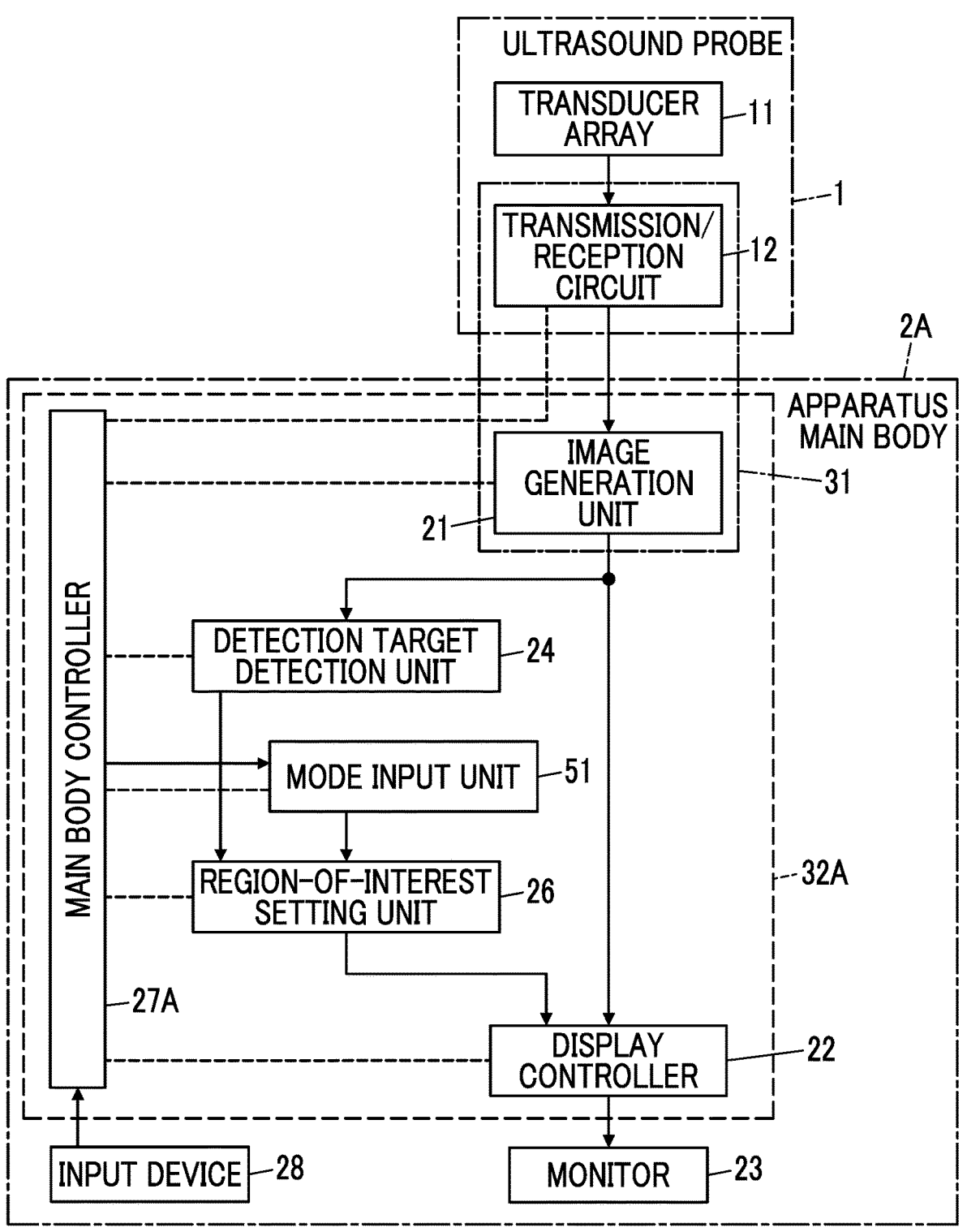
FIG. 10 is a block diagram showing a configuration of an ultrasound diagnostic apparatus according to Embodiment 2 of the present invention.

FIG. 10 shows a configuration of an ultrasound diagnostic apparatus according to Embodiment 2 of the present invention. The ultrasound diagnostic apparatus of Embodiment 2 comprises an apparatus main body 2A instead of the apparatus main body 2 in the ultrasound diagnostic apparatus of Embodiment 1 shown in FIG. 1. The apparatus main body 2A is configured such that the detection target analysis unit 25 is removed, a mode input unit 51 is added, and a main body controller 27A is provided instead of the main body controller 27, with respect to the apparatus main body 2 in Embodiment 1.

In the apparatus main body 2A, the mode input unit 51 is connected to the region-of-interest setting unit 26 and the main body controller 27A. In addition, a processor 32A for the apparatus main body 2A is composed of the image generation unit 21, the display controller 22, the detection target detection unit 24, the region-of-interest setting unit 26, the main body controller 27A, and the mode input unit 51.

The ultrasound diagnostic apparatus of Embodiment 2 has a plurality of examination modes for a plurality of the detection targets A in advance. Here, the examination mode refers to a mode in which examination is performed using presets that are composed of a plurality of conditions, such as a so-called gain condition and a so-called dynamic range condition, set in advance in conformity with a specific detection target A.

The mode input unit 51 inputs, among the plurality of examination modes of the ultrasound diagnostic apparatus, an examination mode for the detection target captured in the ultrasound image U, for example, based on the user's instruction via the input device 28.

The detection target detection unit 24 analyzes the ultrasound image U generated by the image generation unit 21 to detect the detection target A shown in the ultrasound image U. In a case where the examination mode input by the mode input unit 51 is used, the detection target A corresponding to the examination mode can be clearly captured in the ultrasound image U, so that the detection target detection unit 24 can easily detect the detection target A.

The region-of-interest setting unit 26 stores in advance a plurality of detection targets A each of which has brightness in the posterior echo different from the brightness of the surroundings thereof, such as a feces inside the rectum and a cyst, and a plurality of other detection targets A, and sets, on the ultrasound image U, the region of interest to be disposed at a position corresponding the examination mode.

For example, the region-of-interest setting unit 26 can set the first region of interest R1 in a case where the examination mode input from the mode input unit 51 indicates a feces inside the rectum as the detection target A or a cyst as the detection target A, and can set the second region of interest R2 in a case where the examination mode input from the mode input unit 51 indicates an empty rectum as the detection target A or a tumor as the detection target A.

Hereinafter, an example of the operation of the ultrasound diagnostic apparatus according to Embodiment 2 will be described based on the flowchart shown in FIG. 11.

First, in step S11, the mode input unit 51 inputs one of the plurality of examination modes stored in advance in the ultrasound diagnostic apparatus, based on the user's instruction via the input device 28.

Next, in step S12, the user disposes the ultrasound probe 1 at an appropriate position on the body surface of the subject under examination in order to capture the image of the detection target A corresponding to the examination mode set in step S11, and the ultrasound image U is acquired in the same manner as in step S1 in the flowchart of FIG. 8.

In step S13, the detection target A captured in the ultrasound image U is detected by the detection target detection unit 24 in the same manner as in step S2 in the flowchart of FIG. 8.

In step S14, the region-of-interest setting unit 26 sets the region of interest that is to be disposed at a position corresponding to the examination mode set in step S1 and that surrounds the detection target A detected in step S13. For example, in a case where an examination mode corresponding to a feces inside the rectum is set in step S1, the region-of-interest setting unit 26 can set the first region of interest R1 as the region of interest corresponding to the examination mode. In addition, for example, in a case where an examination mode corresponding to an empty rectum is set in step S1, the region-of-interest setting unit 26 can set the second region of interest R2 as the region of interest corresponding to the examination mode.

The first region of interest R1 or the second region of interest R2 set in step S14 is sent to the display controller 22 and can be displayed on the monitor 23, for example, with a closed frame line representing the edge of each region of interest. Since the first region of interest R1 including the region located at the deeper part than the detection target A1 is set for the detection target A1 such as a feces in which the posterior acoustic shadow can be confirmed, the user can easily and accurately perform the diagnosis by clearly confirming the posterior acoustic shadow or the like of the detection target A1.

Figure 11:
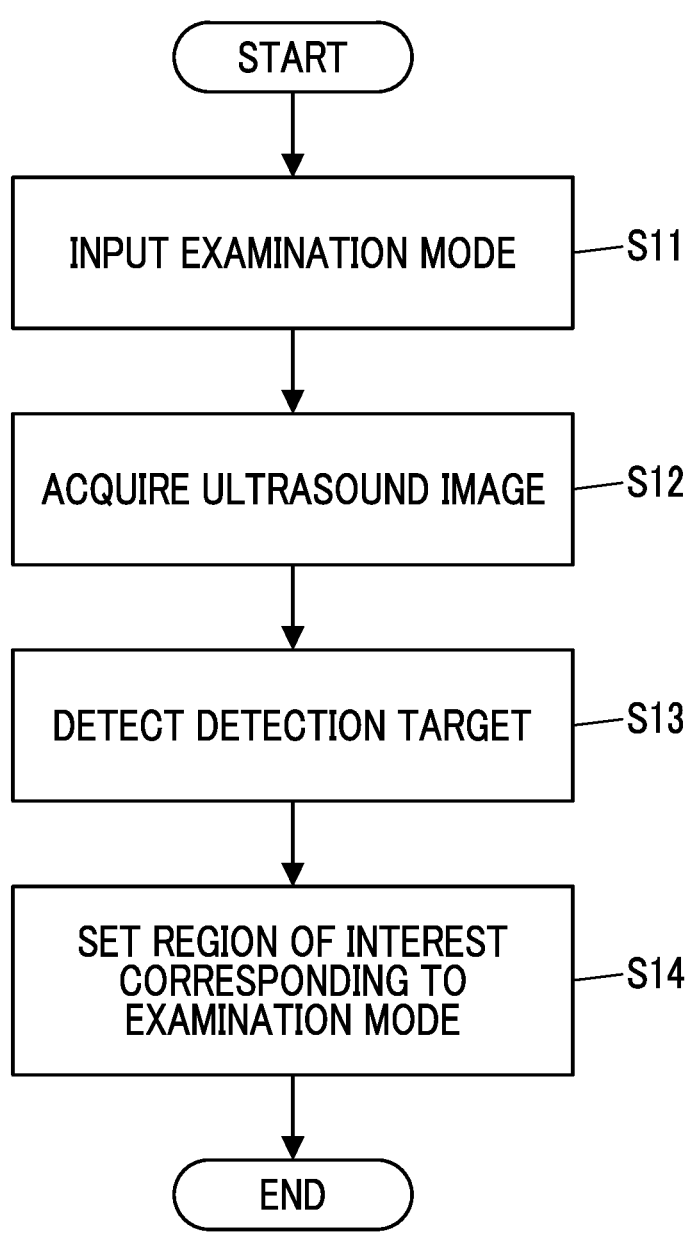
FIG. 11 is a flowchart showing an operation of the ultrasound diagnostic apparatus according to Embodiment 2 of the present invention.

In a case where the processing of step S14 is completed in this way, the operation of the ultrasound diagnostic apparatus shown in FIG. 11 is completed.

As described above, with the ultrasound diagnostic apparatus according to Embodiment 2 of the present invention, the mode input unit 51 inputs the examination mode for the detection target A captured in the ultrasound image U, and the region-of-interest setting unit 26 sets the region of interest to be disposed at a position corresponding to the examination mode input from the mode input unit 51. Therefore, even in a case where it is necessary to confirm the posterior echo of the detection target A, the user can easily and accurately perform the diagnosis related to the detection target A by clearly confirming the posterior echo, similarly to the ultrasound diagnostic apparatus of Embodiment 1.

EXPLANATION OF REFERENCES

1: ultrasound probe
2, 2A: apparatus main body
11: transducer array
12: transmission/reception circuit
21: image generation unit
22: display controller
23: monitor
24: detection target detection unit
25: detection target analysis unit
26: region-of-interest setting unit
27, 27A: main body controller
28: input device
31: image acquisition unit
32, 32A: processor
41: pulsar
42: amplification section
43: AD conversion section
44: beam former
45: signal processing section
46: DSC
47: image processing section
51: mode input unit
A, A1, A2: detection target
B: image region
C: contour line
E1, E2: side
R1: first region of interest
R2: second region of interest
U: ultrasound image

What is claimed is:

1. An ultrasound diagnostic apparatus comprising:
a processor configured to
detect a detection target captured in an ultrasound image,
detect a posterior acoustic shadow of the detection target or an enhanced posterior echo of the detection target, the posterior acoustic shadow or the enhanced posterior echo being included in the ultrasound image,
automatically set, on the ultrasound image, a first region of interest that includes the detection target and the posterior acoustic shadow, or the detection target and the enhanced posterior echo, and of which an edge is represented by a closed frame line that has a side that extends along a sound line of the ultrasound image, and
superimpose the first region of interest on the ultrasound image,
wherein the detection target is located closer to shallower side end of the first region of interest than deeper side end of the first region of interest.

2. The ultrasound diagnostic apparatus according to claim 1,
wherein the processor is further configured to
set the first region of interest for the detection target in which an enhancement of the posterior echo of the detection target is equal to or higher than a predetermined level, and
set a second region of interest of which a position relative to the detection target is different from that of the first region of interest for the detection target in which the enhancement of the posterior echo of the detection target is less than the predetermined level.

3. The ultrasound diagnostic apparatus according to claim 2, wherein the second region of interest is a region having a position relative to the detection target such that the detection target is located in a central part within the second region of interest.

4. The ultrasound diagnostic apparatus according to claim 3, wherein the first region of interest has a length in a depth direction of at least 2 times and no more than 5 times a length of the detection target in the depth direction, and the second region of interest has a length in the depth direction of at least 1 time and less than 2 times the length of the detection target in the depth direction.

5. The ultrasound diagnostic apparatus according to claim 1, wherein the processor is further configured to set the first region of interest for a feces inside a rectum which is the detection target, and set a second region of interest of which a position relative to the detection target is different from that of the first region of interest for an empty rectum which is the detection target.

6. The ultrasound diagnostic apparatus according to claim 5, wherein the second region of interest is a region having a position relative to the detection target such that the detection target is located in a central part within the second region of interest.

7. The ultrasound diagnostic apparatus according to claim 6, wherein the first region of interest has a length in a depth direction of at least 2 times and no more than 5 times a length of the detection target in the depth direction, and the second region of interest has a length in the depth direction of at least 1 time and less than 2 times the length of the detection target in the depth direction.

8. The ultrasound diagnostic apparatus according to claim 1, wherein the processor is further configured to set the first region of interest for a cyst which is the detection target, and set a second region of interest of which a position relative to the detection target is different from that of the first region of interest for a tumor which is the detection target.

9. The ultrasound diagnostic apparatus according to claim 8, wherein the second region of interest is a region having a position relative to the detection target such that the detection target is located in a central part within the second region of interest.

10. The ultrasound diagnostic apparatus according to claim 9, wherein the first region of interest has a length in a depth direction of at least 2 times and no more than 5 times a length of the detection target in the depth direction, and the second region of interest has a length in the depth direction of at least 1 time and less than 2 times the length of the detection target in the depth direction.

11. The ultrasound diagnostic apparatus according to claim 1, further comprising:

an ultrasound probe, and wherein the processor is further configured to acquire the ultrasound image using the ultrasound probe.

12. An ultrasound diagnostic apparatus comprising:

a processor configured to store in advance, with relating each other, a plurality of examination modes corresponding to a plurality of detection targets, and a plurality of sizes of an extended region occupying between each of the plurality of detection targets and a deeper side end of a region of interest, input an examination mode for a captured detection target in an ultrasound image, among the plurality of examination modes, and automatically set, on the ultrasound image, a first region of interest that includes the captured detection target and that has a size of the extended region corresponding to the examination mode, the region of interest having an edge that extends along a sound line of the ultrasound image, wherein the extended region corresponds to a posterior acoustic shadow of the detection target or an enhanced posterior echo of the detection target, the posterior acoustic shadow or the enhanced posterior echo being included in the ultrasound image.

13. The ultrasound diagnostic apparatus according to claim 12, wherein the processor is further configured to set the first region of interest for the examination mode indicating a feces inside a rectum as the detection target or a cyst as the detection target, and set a second region of interest of which a position relative to the detection target is different from that of the first region of interest for the examination mode indicating an empty rectum as the detection target or a tumor as the detection target.

14. The ultrasound diagnostic apparatus according to claim 13, wherein the second region of interest is a region having a position relative to the detection target such that the detection target is located in a central part within the second region of interest.

15. The ultrasound diagnostic apparatus according to claim 14, wherein the first region of interest has a length in a depth direction of at least 2 times and no more than 5 times a length of the detection target in the depth direction, and the second region of interest has a length in the depth direction of at least 1 time and less than 2 times the length of the detection target in the depth direction.

16. The ultrasound diagnostic apparatus according to claim 12, further comprising:

an ultrasound probe, and wherein the processor is further configured to acquire the ultrasound image using the ultrasound probe.

17. A control method for an ultrasound diagnostic apparatus, comprising:

detecting a detection target captured in an ultrasound image;

detecting a posterior acoustic shadow of the detection target or an enhanced posterior echo of the detection target, the posterior acoustic shadow or the enhanced posterior echo being included in the ultrasound image;

automatically setting, on the ultrasound image, a first region of interest that includes the detection target and the posterior acoustic shadow, or the detection target and the enhanced posterior echo, and of which an edge is represented by a closed frame line that has a side that extends along a sound line of the ultrasound image; and superimposing the first region of interest on the ultrasound image, wherein the detection target is located closer to shallower side end of the first region of interest than deeper side end of the first region of interest.

18. A control method for an ultrasound diagnostic apparatus, comprising:

storing in advance, with relating each other, a plurality of examination modes corresponding to a plurality of detection targets, and a plurality of sizes of an extended region occupying between each of the plurality of detection targets and a deeper side end of a region of interest;

inputting an examination mode for a captured detection target in an ultrasound image, among the plurality of examination modes; and automatically setting, on the ultrasound image, the region of interest that includes the captured detection target and that has a size of the extended region corresponding to the input examination mode, the region of interest having an edge that extends along a sound line of the ultrasound image, wherein the extended region corresponds to a posterior acoustic shadow of the detection target or an enhanced posterior echo of the detection target, the posterior acoustic shadow or the enhanced posterior echo being included in the ultrasound image.

* * * * *